US008685189B2

(12) United States Patent
Pamperin et al.

(10) Patent No.: US 8,685,189 B2
(45) Date of Patent: Apr. 1, 2014

(54) PROCESS FOR MAKING A FLEXIBLE MULTI-PANEL STERILIZATION ASSEMBLY

(75) Inventors: Mark T. Pamperin, Cumming, GA (US); Brian L. Gustin, Roswell, GA (US); Eric T. Bricker, Roswell, GA (US); Melissa R. Gaynor, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 320 days.

(21) Appl. No.: 13/338,545

(22) Filed: Dec. 28, 2011

(65) Prior Publication Data

US 2013/0171427 A1    Jul. 4, 2013

(51) Int. Cl.
*B32B 37/00* (2006.01)

(52) U.S. Cl.
USPC ........... 156/73.1; 156/267; 156/269; 156/277

(58) Field of Classification Search
USPC ........ 156/73.1, 256, 263, 264, 265, 267, 269, 156/277
See application file for complete search history.

(56) References Cited

U.S. PATENT DOCUMENTS

| 8,261,963 B2* | 9/2012 | Gaynor et al. ............. 229/87.01 |
| 8,485,419 B2* | 7/2013 | Gaynor et al. ............. 229/87.01 |
| 2011/0033137 A1* | 2/2011 | Gaynor et al. ................ 383/105 |
| 2012/0079795 A1* | 4/2012 | Smith et al. ..................... 53/461 |
| 2012/0202000 A1* | 8/2012 | Bricker et al. .................. 428/99 |
| 2013/0001283 A1* | 1/2013 | Friderich et al. ........... 229/87.01 |
| 2013/0020380 A1* | 1/2013 | Gaynor et al. ............. 229/87.01 |
| 2013/0092724 A1* | 4/2013 | Gaynor et al. ............. 229/87.05 |

FOREIGN PATENT DOCUMENTS

| EP | 2 047 985 A1 | 4/2009 |
| WO | WO 2011/016006 A2 | 2/2011 |

* cited by examiner

*Primary Examiner* — James Sells
(74) *Attorney, Agent, or Firm* — Karl V. Sidor

(57) ABSTRACT

A continuous process for making a multi-panel sterilization assembly, the process including the steps of: providing a moving, continuous base web; providing a plurality of subassemblies; applying the subassemblies in position on the moving, continuous base web to define repeating portions that incorporate the subassemblies and alternating portions that lack such subassemblies; providing side tabs; applying the side tabs in position on the moving, continuous base web with respect to at least one edge of the portions that incorporate the subassemblies; attaching the subassemblies and the side tabs to the moving, continuous base web to form a continuous work-piece; and separating the continuous work-piece into individual multi-panel sterilization assemblies, each multi-panel sterilization assembly comprising a barrier panel, a fold protection panel and at least one side tab.

27 Claims, 5 Drawing Sheets

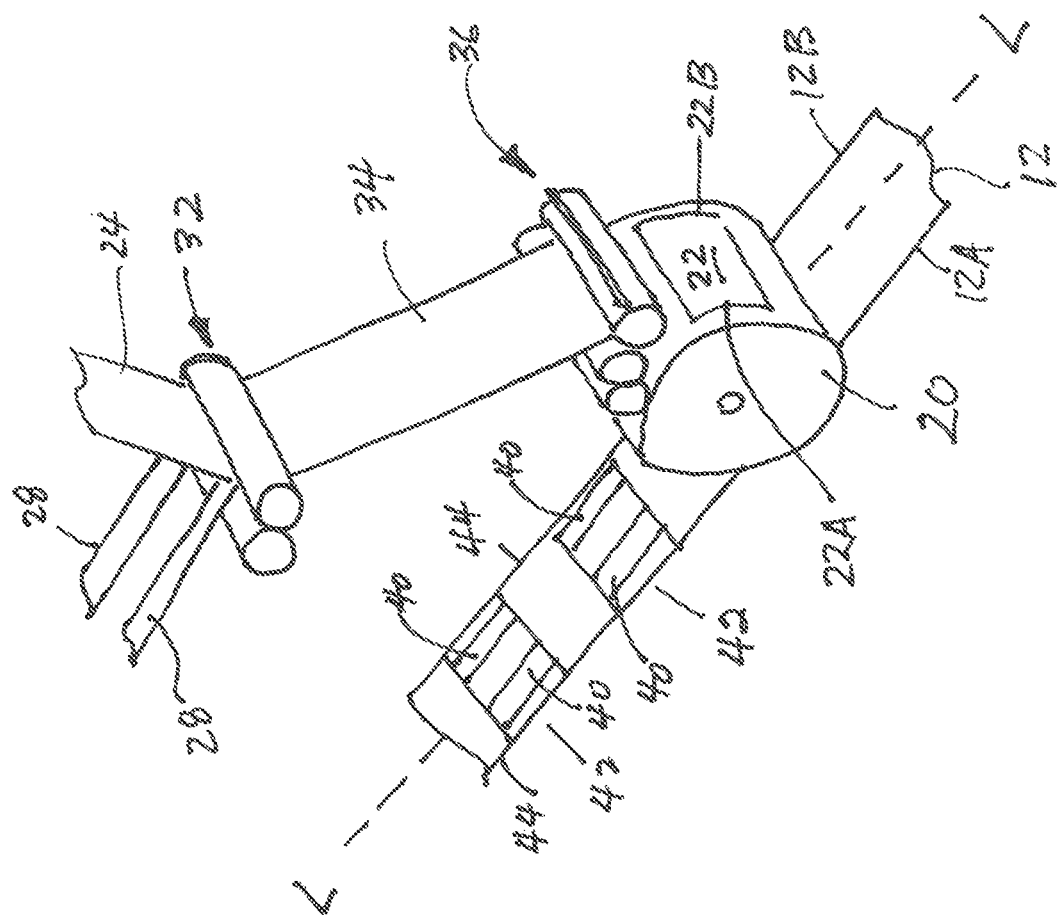

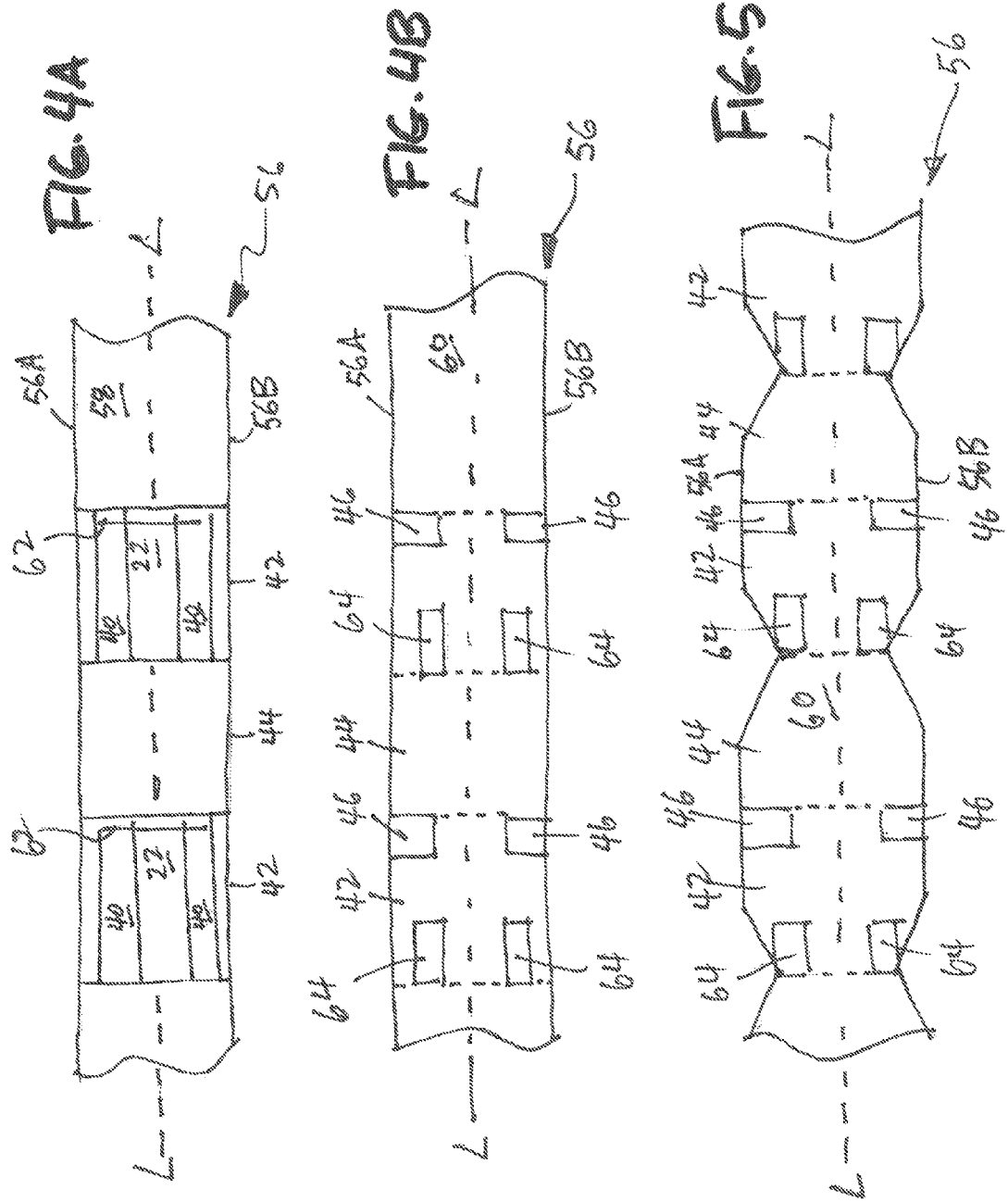

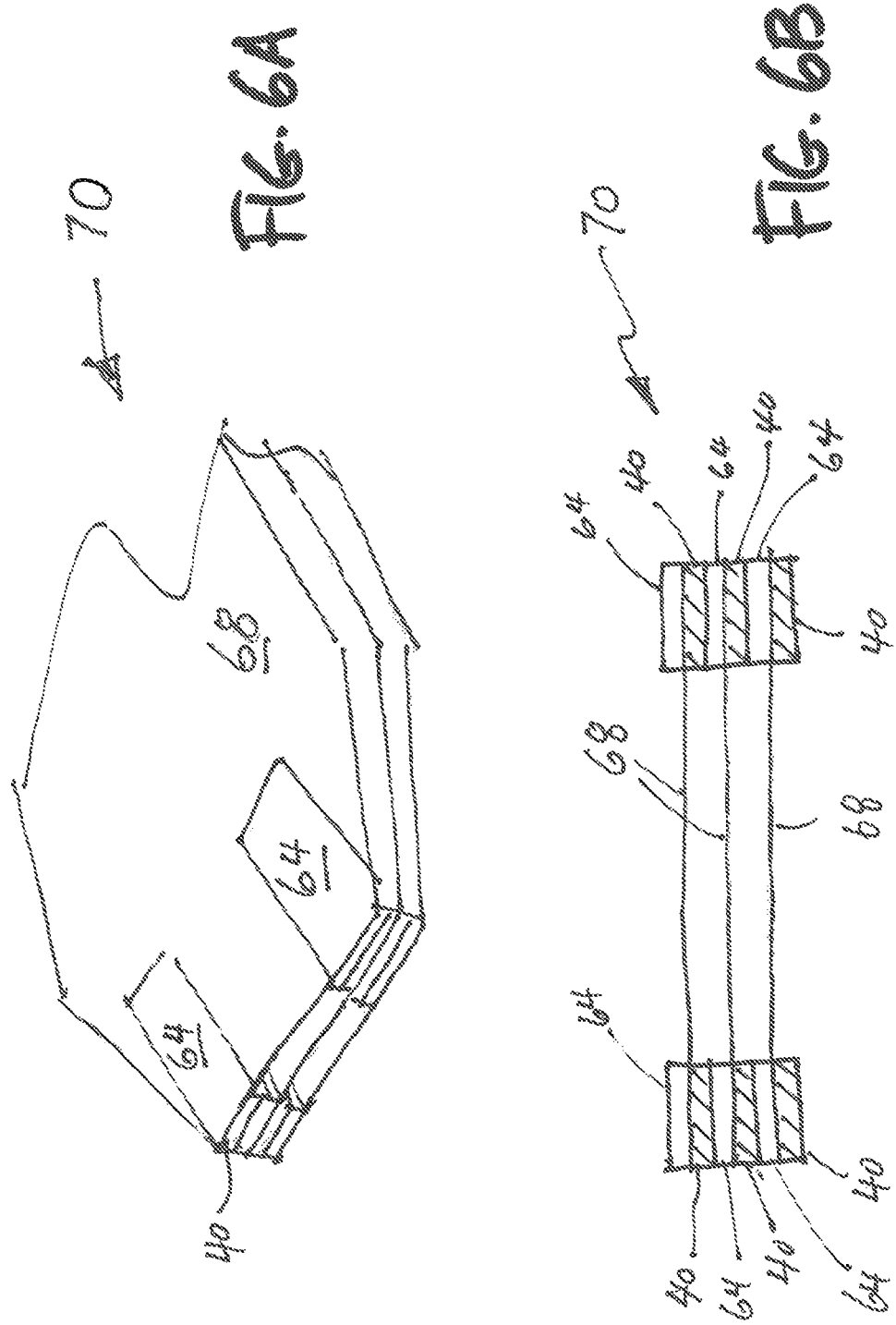

PROCESS FOR MAKING A FLEXIBLE MULTI-PANEL STERILIZATION ASSEMBLY

FIELD OF THE INVENTION

The present invention relates in general to a process for manufacturing a sterilization assembly.

BACKGROUND OF THE INVENTION

A variety of products such as gowns, sheets, drapes, instruments, etc. which are required during surgery or other aseptic procedures, are used on a daily basis in the normal operation of hospitals, clinics and the like. Where such products are not pre-packaged in a sterile state, it is necessary for the hospital or clinic to sterilize them before use. Furthermore, where these products are not disposable, and are employed more than once, it is necessary that they be cleaned and otherwise prepared for subsequent use. Prior to such use, however, it is essential that such products be sterilized.

Due to the volume of materials involved, it is often necessary to sterilize and store these products for later use. Accordingly, there has been developed a procedure where such products, after cleaning, laundering and the like, are wrapped in sterilization fabric and then sterilized and stored for subsequent use. Disposable sterilization fabric is typically cut into predetermined rectangular shapes and sold as sterilization wraps.

Traditional wrapping of a sterilization tray or similar articles in a conventional disposable sterilization wrap often involves a large amount of redundant material as excess corners and overlapping plies are gathered, folded, and secured together at the top of the sterilization tray. Conventional disposable sterilization wrap is a flat, featureless sheet of material that may occasionally contain one or more additional layers of material for strength or absorbency. For example, U.S. Pat. No. 5,635,134 to Bourne, et al. discloses a multi-ply sterilization wrap which is formed by joining one or more sheets of sterilization wrap (e.g., two separate sheets or one sheet folded over) together to form two similarly sized, superposed panels that allow convenient dual wrapping of an article. As another example, U.S. Patent Application Publication No. 2001/0036519 by Robert T. Bayer discloses a two ply sterilization wrap that is formed of a single sheet of sterilization wrap material which is folded to form two similarly sized, superposed panels that are attached to each other. As yet another example, U.S. Patent Application Publication No. 2005/0163654 by Stecklein, et al. discloses a sterilization wrap material that has a first main panel and a second panel that is smaller than the main panel. The second panel is superposed and attached to the central portion of the main panel such that it is contained entirely within the main panel to reinforce the main panel and/or provide additional absorbency.

Generally speaking, in these and other examples, conventional disposable sterilization wraps are readily manufactured by very simple processes involving overlaying two sheets of material or folding a single piece of material to form two sheets and then attaching the sheets together forming a unitary wrap.

Large sheets of conventional disposable sterilization wrap in combination with standard fold techniques do provide an advantage during unwrapping of an item after sterilization, particularly when the sterilization wrap is formed from a material that may stiffen or take a set during the sterilization process. For example, when sterilization wrap composed of nonwoven material made from certain thermoplastic polymers are used in an extended or enhanced steam or heat sterilization process, the nonwoven material may set or "imprint" the shape of the wrapped article or tray. During unwrapping of the article or tray, imprinted creases, folds or other deformations must be overcome during unfolding so the sterilization wrap can lay flat. If the sterilization wrap does not lie flat, it is possible for unfolded sides of the sterilization wrap to fold back up over the sterilized article or tray while other portions of the wrap are being unfolded. This would compromise the sterility of the article. The large expanses of material and the rectangular shape of the sheets in combination with standard folding techniques generally keep the sterilization wrap from folding back onto itself during unwrapping.

When these large sheets of conventional sterilization wrap are reduced in size, the reduction in material amplifies the problem of unfolded sides of the sterilization wrap folding back up over the sterilized article or tray while other portions of the wrap are being unfolded. Moreover, this problem can also be amplified by altering the geometry of the sheet of sterilization wrap so the sheet is no longer rectangular (e.g., in order to reduce the amount of material in the sheet). However, the use of large sheets of conventional disposable sterilization wrap with standard fold techniques provides large expanses of overlapping materials and multiple folds which require using and manipulating excessive amounts of material during the wrapping and unwrapping process, adding difficulty that slows the wrapping and unwrapping process, and creating waste.

Accordingly, there is an unmet need for a process to make an easy to use assembly, package or system that reduces the amount of sterilization fabric needed for the sterile processing of an instrument tray or article. There is also an unmet need for a process to make an easy to use assembly, package or system that reduces the amount of sterilization fabric and simplifies the task of unwrapping a sterilized instrument tray or article while reducing or avoiding the likelihood that the sterilization fabric will fold back onto itself during unwrapping. The need is particularly apparent for process to make an assembly, package or system having multiple panels and other components that reduce the amount of sterilization fabric, that can be used in an extended or enhanced steam or heat sterilization process, and that simplifies the task of unwrapping a sterilized instrument tray or article while reducing or avoiding the likelihood that the sterilization fabric will fold back onto itself during unwrapping.

BRIEF SUMMARY OF THE INVENTION

The problems described above are addressed by the present invention which encompasses a continuous process for making a multi-panel sterilization assembly.

The process involves providing a moving, continuous base web. The continuous base web has a longitudinal centerline and at two opposed edges generally parallel with the centerline.

A plurality of subassemblies is provided, each subassembly having at least two opposed edges and a barrier component. The plurality of subassemblies may be provided by unwinding a roll of material and separating the material into individual subassemblies. Alternatively, a stack of individual subassemblies may be provided. In an aspect of the invention, at least one reinforcement element may be included with each subassembly. For example, at least one reinforcement element may be registered and attached with each subassembly. For another example, a portion of the each subassembly is folded over itself between the two opposed edges to form at least one reinforcement element.

The subassemblies are positioned on the continuous base web so that the at least two opposed edges of each subassembly are aligned with the two opposed edges of the continuous base web to define repeating portions that incorporate the subassemblies and alternating portions that lack such subassemblies. The repeating portions with subassemblies are barrier panel portions and the alternating portions that lack subassemblies are fold protection panel portions. As described in more detail below, alignment of the subassembly and base web encompasses configurations in which an edge of a subassembly extends beyond an edge of the base web in a generally parallel manner and/or configurations in which an edge of the base web extends beyond the edge of a subassembly in a generally parallel manner.

The process includes the step of providing side tabs. These side tabs are registered in position on the moving, continuous base web with respect to at least one edge of the portions that incorporate the subassemblies. For example, the side tabs may be accelerated and registered in position.

The subassemblies and the side tabs are attached to the continuous base web to form a continuous work-piece. This continuous work-piece has two opposed edges and barrier panel portions coinciding with the subassemblies and fold protection panel portions coinciding with the portions lacking subassemblies. The continuous work-piece has a first surface including the subassemblies and an opposed second surface. The subassemblies and/or side tabs may be attached to the continuous base web utilizing ultrasonic bonding techniques. Alternatively and/or additionally, thermal bonding, adhesive bonding, stitching, mechanical engagement or the like may be used to attach these components together. The subassemblies and/or side tabs may be attached to the continuous base web in sequence. For example, the subassemblies may be bonded to the moving continuous base web and then the side tabs may be bonded to become part of the continuous work-piece. Alternatively, the subassemblies and side tabs may be bonded to the continuous base web simultaneously.

The individual side tabs may be attached to the first surface, the second surface, or to both the first and second surfaces. In an aspect of the invention, the step of providing side tabs may include providing side tabs having barrier panel attachment means. These barrier panel attachment means may be adhesive tape, double-sided adhesive tape, cleavable release tapes, layered release tapes, cohesive materials, hook components of hook-and-loop fastening systems, mechanical fastening components including, but not limited to, snaps, clips, magnets, catches, slots and tabs, and combinations thereof.

The continuous work-piece is then separated into individual multi-panel sterilization assemblies with each multi-panel sterilization assembly including a barrier panel, a fold protection panel and at least a side tab.

According to an aspect of the invention, the process may include the step of adding indicia to the barrier panel, the indicia identifying an upper boundary of a content receiving region of the barrier panel. The indicia may be added to the subassembly before the subassembly is attached to the continuous base web. Alternatively and/or additionally, the indicia may be added to the barrier panel portion of the continuous work-piece after the subassembly is attached to the continuous work-piece. In yet another aspect, the indicia may be added to the barrier panel of the multi-panel sterilization assembly.

The process of the present invention may further include the step registering at least one pull tab in position on the barrier panel portion of the moving, continuous base web and then attaching the pull tab. For example, the pull tab may be accelerated and registered in position. The pull tab may be attached to the second surface or the first surface. It is contemplated that the pull tab may be attached to both the first and second surfaces. According to the invention, the pull tab may desirably be bonded to the moving, continuous base web along with the subassemblies and the side tabs. Alternatively and/or additionally, the process may involve the step of registering in position and attaching at least one pull tab in position on the barrier panel of an individual multi-panel sterilization assembly either before or after the individual assembly is separated from the continuous work-piece.

According to aspects of the invention, portions of the edges of the continuous work-piece may be cut to create a shape prior to the step of separating the continuous work-piece into individual multi-panel sterilization assemblies. For example, portions of the continuous work-piece may be cut out from the two opposed edges toward the longitudinal centerline prior to the step of separating the continuous work-piece into individual multi-panel sterilization assemblies.

The process of the present invention may further include the step of collating multi-panel sterilization assemblies into a stack and folding the stack. In an aspect of the invention, the multi-panel sterilization assemblies include reinforcement elements and at least one pull tab and the multi-panel sterilization assemblies are collated so that the barrier panels are superposed in the stack and the reinforcement elements and pull tabs create a separation between adjoining multi-panel sterilization assemblies in the stack for a user to insert one or more fingers to grip one or more individual multi-panel sterilization assemblies in the stack.

The present invention also encompasses a continuous process for making a multi-panel sterilization assembly utilizing a discrete base web instead of a continuous base web. Such a process involves providing a subassembly that includes at least two opposed edges and a barrier panel component spanning between the two opposed edges. The subassembly may be provided by unwinding a roll of material and cutting the material into individual subassemblies. Alternatively, a stack of individual subassemblies may be provided. In an aspect of the invention, at least one reinforcement element may be included with each subassembly. For example, at least one reinforcement element may be registered in position and attached to each subassembly.

The subassembly is registered in position on a discrete base web. This discrete base web has a leading end, a trailing end, and two opposed edges generally perpendicular to the leading and trailing ends such that the at least two opposed edges of a subassembly are aligned, e.g. to coincide and/or to be spaced-away in a generally parallel fashion, with the two opposed edges of the base web to define a discrete work-piece including a barrier panel portion incorporating the subassembly and a fold protection panel portion lacking the subassembly. The work-piece has a first surface including the subassembly and an opposed second surface. Desirably, the discrete work-piece is supported on a belt or conveyor or it may be supported on or integrated with a carrier web.

The process includes the step of providing one or more side tabs. These side tabs are registered in position with respect to at least one edge of the barrier panel portion of the work-piece.

The subassembly and the side tab(s) are attached to the base web to provide a multi-panel sterilization assembly including a barrier panel, a fold protection panel and at least one side tab. The subassembly and/or side tabs may be attached to the base web utilizing ultrasonic bonding techniques. Alternatively and/or additionally, thermal bonding, adhesive bonding, stitching, mechanical engagement or the like may be used to attach these components together. The subassembly and/or side tabs may be attached to the base web in sequence. For example, the subassembly may be attached to the base web and then the side tabs may be attached to the base web. Alternatively, the subassembly and side tabs may be attached to the base web simultaneously.

The individual side tabs may be attached to the first surface, the second surface, or to both the first and second surfaces. In an aspect of the invention, the step of providing side tabs may include providing side tabs having barrier panel attachment means. These barrier panel attachment means may be adhesive tape, double-sided adhesive tape, cleavable release tapes, layered release tapes, cohesive materials, hook components of hook-and-loop fastening systems, mechanical fastening components including, but not limited to, snaps, clips, magnets, catches, slots and tabs, and combinations thereof.

According to an aspect of the invention, the process may include the step of adding indicia to the barrier panel, the indicia identifying an upper boundary of a content receiving region of the barrier panel. The indicia may be added to the subassembly before the subassembly is attached to the base web. Alternatively and/or additionally, the indicia may be added to the barrier panel portion of the discrete work-piece after the subassembly is attached to the work-piece. In yet another aspect, the indicia may be added to the barrier panel of the multi-panel sterilization assembly.

The process of the present invention may further include the step of registering at least one pull tab in position on the base web and then attaching the pull tab. The pull tab may be attached to the second surface or the first surface. It is contemplated that the pull tab may be attached to both the first and second surfaces. According to the invention, the pull tab may be attached to the base web along with the subassembly and the side tab(s). Alternatively and/or additionally, the process may involve the step registering at least one pull tab in position on the barrier panel of a multi-panel sterilization assembly and then attaching the pull tab.

According to aspects of the invention, portions of the edges of the work-piece may be cut to create a shape for the multi-panel sterilization assembly. For example, portions may be cut out from the two opposed edges (or other edges) of the work-piece. Alternatively and/or additionally, portions may be cut from the multi-panel sterilization assembly to change its shape or trim material.

The process of the present invention may further include the step of collating multi-panel sterilization assemblies into a stack and folding the stack. In an aspect of the invention, the multi-panel sterilization assemblies include reinforcement elements and at least one pull tab and the multi-panel sterilization assemblies are collated so that the barrier panels are superposed in the stack and the reinforcement elements and pull tabs create separations between adjoining multi-panel sterilization assemblies in the stack to provide gaps for a user to insert one or more fingers to grip one or more individual multi-panel sterilization assemblies in the stack.

The present invention also encompasses a stack of multi-panel sterilization assemblies and a process of making the same. The stack includes a plurality of multi-panel sterilization assemblies that each includes a barrier panel, a fold protection panel, a reinforcement element and at least one pull tab. The stack is collated so that the barrier panels are superposed in the stack, whereby the reinforcement elements and pull tabs create separations between adjoining multi-panel sterilization assemblies in the stack to provide gaps for a user to insert one or more fingers to grip and separate one or more of the multi-panel sterilization assemblies from the stack.

Other objects, advantages and applications of the present disclosure will be made clear by the following detailed description of a preferred embodiment of the disclosure and the accompanying drawings wherein reference numerals refer to like or equivalent structures.

DESCRIPTION OF THE DRAWINGS

FIG. 3 is a perspective view illustrating a detail of an exemplary process for making a multi-panel sterilization assembly.

FIG. 4A is a top plan view of an exemplary work-piece from an exemplary process for making a multi-panel sterilization assembly.

FIG. 4B is a bottom plan view of an exemplary work-piece from an exemplary process for making a multi-panel sterilization assembly.

FIG. 5 is a bottom plan view illustrating a detail of an exemplary work-piece from an exemplary process for making a multi-panel sterilization assembly.

FIG. 6A is a perspective view of an exemplary stack of multi-panel sterilization assemblies.

FIG. 6B is a side view illustrating a detail of an exemplary stack of multi-panel sterilization assemblies.

DEFINITIONS

Figure 1:
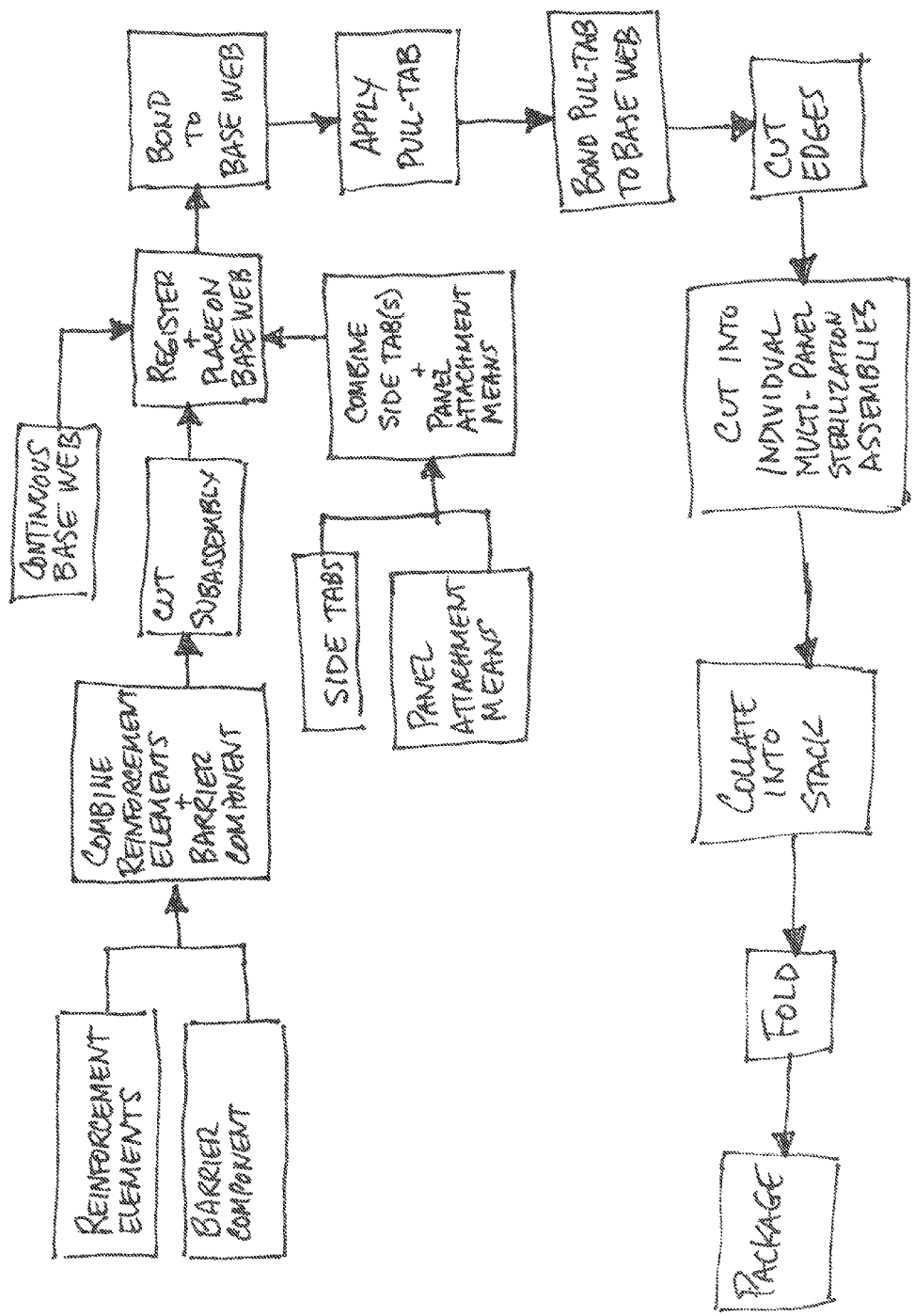
FIG. 1 is a schematic illustration of an exemplary process for making a multi-panel sterilization assembly.

As used herein, the term "disposable" refers to a product that is so inexpensive that it may economically be discarded after only a single use. Products that are "disposable" are typically intended for single use. The term "single-use" refers to a product that is intended to be used for only once and is not intended to be re-used, re-conditioned, restored or repaired after that use. These products offer advantages in clinical settings by reducing the potential for contamination or infection. In addition, these products can enhance work flow since they are not collected and assembled for reprocessing and reuse.

As used herein, the term "sterilization assembly" refers to a flexible article composed of fabric(s) and/or flexible material(s) that is wrapped around, folded around or otherwise encloses a non-sterile article or non-sterile content prior to sterilization. A sterilization assembly has multiple panels and/or sections providing specific physical properties, functional characteristics and/or structure that provide advantages for wrapping or folding, handling, strength, sterilization, storage after sterilization, and/or unwrapping or unfolding.

As used herein, the terms "web" or "nonwoven web" refers to a coherent structure of individual fibers or filaments which are interlaid, but not in an identifiable repeating manner. Nonwoven webs have been, in the past, formed by a variety of processes known to those skilled in the art such as, for example, meltblowing, spunbonding and bonded carded web processes. The term "web" or "nonwoven web" encompasses laminate materials including one or more webs as combinations of woven fabrics and nonwoven webs and/or combinations of nonwoven webs and films.

As used herein, the terms "spunbond web" or "spunbonded web" refer to a web of small diameter fibers and/or filaments which are formed by extruding a molten thermoplastic material as filaments from a plurality of fine, usually circular, capillaries in a spinnerette with the diameter of the extruded filaments then being rapidly reduced, for example, by non-eductive or eductive fluid-drawing or other well-known spun-bonding mechanisms. The production of spunbonded non-woven webs is illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714.

As used herein, the term "meltblown fibers" means fibers formed by extruding a molten thermoplastic material through a plurality of fine, usually circular, die capillaries as molten threads or filaments into a high-velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents and publications, including NRL Report 4364, "Manufacture of Super-Fine Organic Fibers" by V. A. Wendt, E. L. Boone, and C. D. Fluharty; NRL Report 5265, "An Improved device for the Formation of Super-Fine Thermoplastic Fibers" by K. D. Lawrence, R. T. Lukas, and J. A. Young; and U.S. Pat. No. 3,849,241, issued Nov. 19, 1974, to Buntin, et al.

As used herein, "ultrasonic bonding" means a process performed, for example, by fusing layers or fibers, desirably thermoplastic layers or fibers, together by application of ultrasonic energy. One non-limiting example of ultrasonic boding is bonding obtained by passing the fabric between a sonic horn and anvil roll as illustrated in U.S. Pat. No. 4,374,888 to Bornslaeger, the entire contents of which is incorporated herein by reference.

As used herein "thermal bonding" means fusing layers or fibers, desirably thermoplastic layers or fibers, together through the direct application of heat. One form of thermal bonding is thermal "point bonding" in which one or more layers of fabric are joined at a plurality of discrete bond points. For example, thermal point bonding generally involves passing a fabric or web of fibers to be bonded between a heated roll assembly such as, for example, a heated calender roll and an anvil roll. Point bonding may also be accomplished using high pressures that fuse layers or fibers together. The calender roll is usually patterned in some way so that the entire fabric is not attached across its entire surface, and the anvil roll is usually smooth. As a result, various patterns for calender rolls have been developed for functional and/or aesthetic reasons. One example of a pattern has points and is the Hansen Pennings or "H&P" pattern with about a 30% bond area with about 200 bonds/square inch (31 bonds/square cm) as taught in U.S. Pat. No. 3,855,046 to Hansen and Pennings. Another example is shown in U.S. Design Pat. No. 239,566 to Vogt. Typically, the percent bonding area varies from around 5% to around 30% of the area of the fabric laminate web. Point bonding holds the laminate layers together as well as imparts integrity to each individual layer by bonding filaments and/or fibers within each layer without destroying the breathability or hand of the fabric.

As used herein, the terms "align" and "alignment" refer to the adjustment of components so they are in proper relative position. With respect to subassembly edges and base web edges, these terms refer to the adjustment of these components such that the edges generally coincide. These terms also encompass configurations in which these edges are "spaced-away" or "spaced-apart" or offset in a generally parallel fashion or in which these edges on one side of the longitudinal centerline coincide and the opposite edges are spaced-away, spaced-apart or offset in a generally parallel fashion. One non-limiting example of spaced-away edge alignment is when an edge of a subassembly extends beyond an edge of the base web; another non-limiting example is when an edge of the base web extends beyond the edge of a subassembly.

DETAILED DESCRIPTION

Reference will now be made in detail to one or more embodiments, examples of which are illustrated in the drawings. It should be understood that features illustrated or described as part of one embodiment may be used with another embodiment to yield still a further embodiment.

Turning now to the drawings, there is shown at FIG. 1 an exemplary process for making a multi-panel sterilization assembly. The exemplary process may be configured for a continuous base web or a discrete base web. The process illustrated schematically by FIG. 1 shows a continuous base web which may be unwound from a roll of material.

The process continues with material for a barrier component being unwound from a roll. Optionally, material for reinforcement elements to be located on the barrier component may also be unwound from a roll and combined with the barrier component by attaching to form a laminate structure. The barrier component, with or without the optional reinforcement elements, may be separated, e.g. cut, to create discrete subassemblies. Alternatively, the subassemblies may be provided as a stack instead of being unwound and separated. The subassemblies are registered and placed on the base web. Side tabs, which may be combined with optional barrier panel attachment means, are registered and placed on the base web. These components (e.g., the subassemblies and the side tabs) are attached to permanently to the base web. The components may be initially secured in position on the moving web with use of a light adhesive prior to being permanently attached, e.g. via thermal and/or ultrasonic bonding. Alternatively, a heavy application of adhesive may be used if attaching the components is to be achieved by adhesive bonding.

A pull tab is applied in position on the base web and then attached in place. The pull tab may be applied along with the side tabs and subassemblies and all the components may be attached simultaneously.

Edges of the base web incorporating these components may be trimmed before the continuous web is separated into individual multi-panel sterilization assemblies that are collated and stacked. The stack is desirably packaged for shipment.

At locations of introductions of discrete components into the process, inspection can take place to determine the presence or absence of acceptable component introduction. In addition to visual inspection, operational characteristics such as start-up/ramp-up/shut-down operations can trigger waste minimization techniques. At each of the operations or steps shown in FIG. 1, diagnostics can be performed to indicate whether contributions to the work-piece meet acceptable criteria. If so, components such as the subassembly, side tabs, pull-tabs, etc., may continue to be applied as shown in FIG. 1. If not, no additional components are applied.

Figure 2:
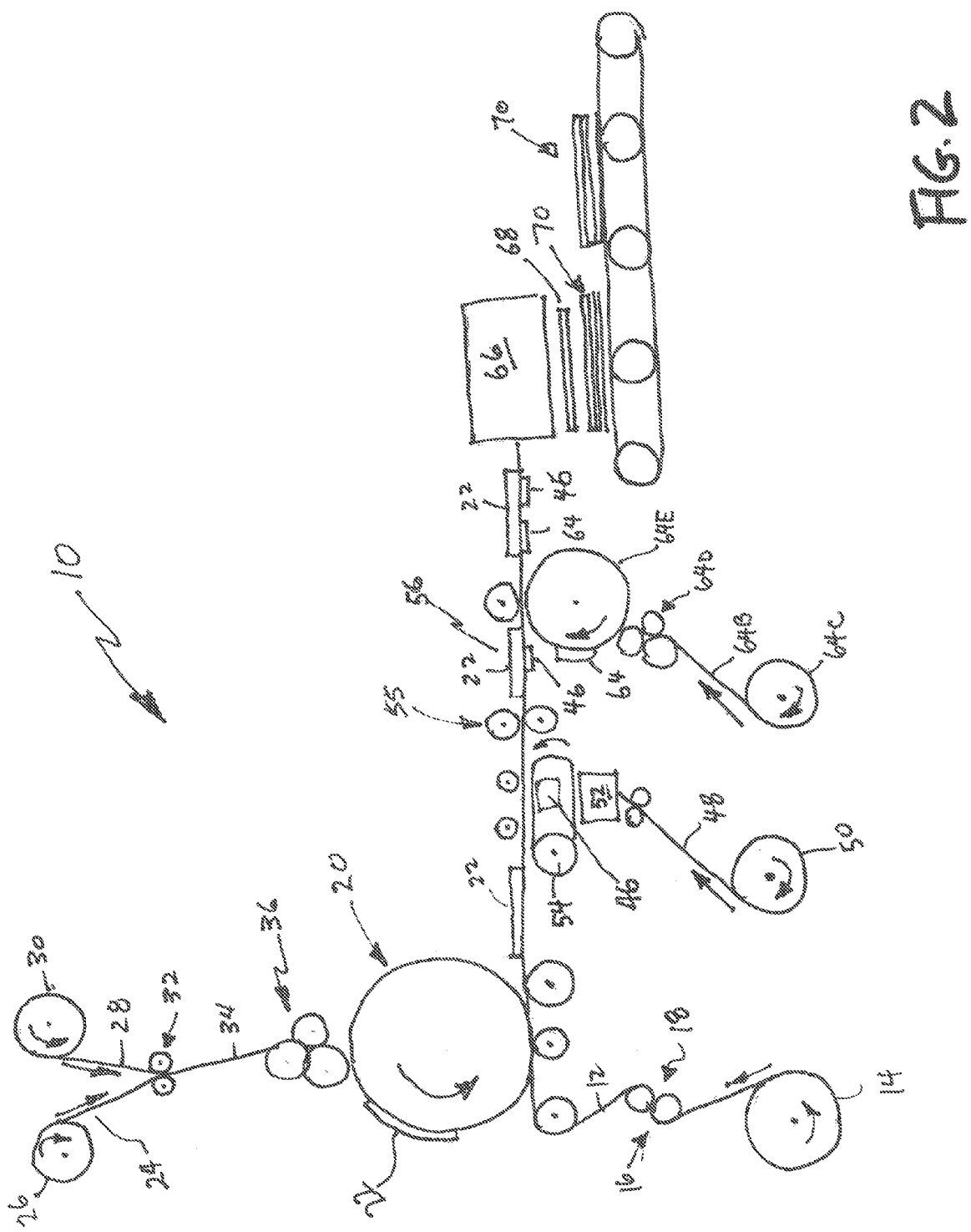
FIG. 2 is a schematic illustration of an exemplary process for making a multi-panel sterilization assembly.

Referring now to FIG. 2, a process 10 for making a multi-panel sterilization assembly is shown schematically. While the invention will be described in connection with desired or preferred embodiments, it will be understood that it is not intended to limit the invention to those embodiments.

According to the present invention, a continuous base web 12 is unwound from a supply roll 14 and travels in the direction indicated by the arrow associated therewith as the supply roll 14 rotates in the direction of the arrows associated therewith. The base web 12 may be formed by one or more sheet making processes and passed directly into the process 10 without first being stored on a supply roll 14. Exemplary sheet-making processes include processes such as meltblowing processes, spunbonding processes, bonded-carded web-making processes, wet-laying processes, apertured film-forming processes, and the like. The continuous base web 12 has a longitudinal centerline "L" and at two opposed edges 12A and 12B generally parallel with the longitudinal centerline L. It is contemplated that a discrete base web may be used instead of a continuous base web. The discrete base web may be supported on a conveyor, a belt, a fabric or a carrier material such as a continuous web of spunbond material. It is contemplated that the carrier material may become part of the finished product after processing.

The base web 12 passes through the nip 16 of an S-roll arrangement 18 in a reverse-S path. From the S-roll arrangement 18, the base web 12 passes to a combining drum 20 which is used to register and place a subassembly 22 on the base web 12. Each subassembly 22 has at least two opposed edges 22A and 22B and a barrier component. In an aspect of the invention, at least one reinforcement element 40 may be included with each subassembly 22.

Generally speaking, the subassembly 22 is formed by unwinding a barrier component material 24 from a supply roll 26 and travels in the direction indicated by the arrow associated therewith as the supply roll 26 rotates in the direction of the arrows associated therewith. The subassembly may include optional reinforcement elements. One way to include the reinforcement elements is to unwind one or more rolls of reinforcement element material 28 from a supply roll 30 that travels in the direction indicated by the arrow associated therewith and position the reinforcement element material 28 against the barrier component material 24 by passing both materials 28, 24 through nip arrangement 32. Another way to include the reinforcement elements is to fold a portion or portions of barrier component material 24 in the direction of travel indicated by the arrow associated with the supply roll 26 via a folding board (not shown) that is positioned between the supply roll 26 and the combining drum 20. The barrier component material and/or the reinforcement element material may be formed by one or more sheet making processes and passed directly into the process 10 without first being stored on a supply roll. Exemplary sheet-making processes include processes such as meltblowing processes, spunbonding processes, bonded-carded web-making processes, wet-laying processes, apertured film-forming processes, and the like.

Referring to FIGS. 2 and 3, the barrier component material 24 and reinforcement element material 28 travels to a nip of a bonding roll arrangement 32 where the materials are attached together. The materials may be attached using conventional techniques. Examples of techniques include, but are not limited to, ultrasonic bonding, thermal bonding, pressure bonding, hot melt adhesives, double-sided tape, transfer adhesives or the like. These combined materials 34 travel to a rotary knife cutting roll 36 arrangement where an individual subassembly 22 is cut and then placed on a combining drum 20. Other techniques may be used to separate the subassembly. Exemplary techniques include a rotary die, lasers, water jets or the like.

The combining drum 20 holds the subassembly 22 on the drum surface using conventional techniques such as, for example, suction. Other techniques may be used to register the subassembly in position and transfer it to the base web. These include transfer pucks, belt placement assemblies or the like. Non-limiting examples of suitable apparatus and methods include those described in U.S. Pat. Nos. 5,716,478 and 5,759,340, both to Boothe et al., the contents of which are incorporated herein by reference. Alternatively, a stack of individual subassemblies 22 may be provided and the individual subassemblies may be fed to the combining drum (or other registration and transfer equipment using conventional techniques).

The subassembly 22 is transferred to the continuous web 12 in a transfer step. The surface of subassembly 22 that is to face the continuous web or a portion of the continuous web 12 that is to receive the subassembly 22 may include a light coating of an adhesive (not shown) to maintain the subassembly in position on the continuous web 12.

According to the present invention, the base web 12 and/or the subassembly 22 may be composed of at least one layer of a breathable nonwoven material. Desirably, the breathable nonwoven material is a laminate composed of a layer of spunbonded filaments, a layer of meltblown fibers, and a layer of spunbonded filaments—also called spunbonded-meltblown-spunbonded material. The method of making these layers is known and described in commonly assigned U.S. Pat. No. 4,041,203 to Brock et al which is incorporated herein in its entirety by reference. The material of Brock et al is a three layer laminate of spunbonded-meltblown-spunbonded layers which is also commonly referred to by the acronym "SMS". The two outer layers of SMS are a spunbonded material made from extruded polyolefin fibers, or filaments, laid down in a random pattern and then attached to one another. The inner layer is a meltblown layer also made from extruded polyolefin fibers generally of a smaller diameter than the fibers in the spunbonded layers. As a result, the meltblown layer provides increased barrier properties due to it fine fiber structure which permits the sterilizing agent to pass through the fabric while preventing passage of bacteria and other contaminants. Conversely, the two outer spunbonded layers provide a greater portion of the strength factor in the overall laminate. The laminate may be prepared using an intermittent bond pattern that is preferably employed with the pattern being substantially regularly repeating over the surface of the laminate. The pattern is selected such that the bonds may occupy about 5-50% of the surface area of the laminate. Desirably, the bonds may occupy about 10-30% of the surface area of the laminate. Other combinations and variations of these materials are contemplated. As a non-limiting example, the inner layer may contain two meltblown layers such that the material may be called "SMMS".

When the base web 12 and/or the subassembly 22 is composed of or incorporates SMS material(s), the basis weight of the SMS material(s) may be from 1 ounce per square yard or "osy" which is approximately (33 grams per square meter or "gsm") to about 3 osy (100 gsm). For example, the basis weight of the SMS material(s) may be from 1.2 osy (40 gsm) to about 2 osy (67 gsm). As another example, the basis weight of the SMS material(s) may be from 1.4 osy (47 gsm) to about 1.8 osy (60 gsm). The basis weight may be determined in accordance with ASTM D3776-07. Multiple plies or layers of SMS material may be used to provide basis weights ranging from about 2 osy (67 gsm) to about 5 osy (167 gsm).

The permeability of the base web and/or the subassembly (or the combined components as a barrier panel portion described hereinafter as barrier panel portion 42) may range from 25 to about 500 cubic feet per minute (CFM) as characterized in terms of Frazier permeability. For example, the permeability of the barrier panel portion may range from 50 to about 400 cubic feet per minute. As yet another example, the permeability of the barrier panel portion may range from 100 to about 300 cubic feet per minute. The Frazier permeability, which expresses the permeability of a material in terms of cubic feet per minute of air through a square foot of area of a surface of the material at a pressure drop of 0.5 inch of water (or 125 Pa), was determined utilizing a Frazier Air Permeability Tester available from the Frazier Precision Instrument Company and measured in accordance with Federal Test Method 5450, Standard No. 191A. When the barrier panel is composed of or incorporates SMS material(s) having basis weights ranging from about 1 osy (33 gsm) to about 2.6 osy (87 gsm), the permeability of the barrier panel portion may range from about 20 cubic feet per minute to about 75 cubic feet per minute when determined generally in accordance with ISO 9237:1995 (measured with an automated air permeability machine using a 38 cm$^2$ circular test area (e.g., test head) at a test pressure of 125 Pa,—exemplary air permeability machine is TEXTEST FX 3300 available from TEXTEST AG, Switzerland). If multiple plies or layers of SMS material are used to provide basis weights ranging from about 2 osy (67 gsm) to about 5 osy (167 gsm), the permeability of the barrier panel may range from about 10 cubic feet per minute to about 30 cubic feet per minute when determined generally in accordance with ISO 9237:1995.

Generally speaking, the material of the base web 12 and the barrier component material 24 of the subassembly 22 may be of the same material or they may be different materials. For example, the base web 12 may be single layer or multiple layers of spunbond nonwoven material, a lightweight nonwoven laminate material, or a material that lacks the level of barrier properties (or other characteristics) that may be desired for the barrier panel portion. Alternatively, the base web may be an "SMS" material. The barrier component material 24 may have a higher level of barrier properties than the base web 12. Alternatively, it is contemplated that the base web 12 may have a higher level of barrier properties than the barrier component material 24. For example, the base web 12 may be a laminate of nonwoven fabrics such as "SMS" material. The base web 12 may have a different color and/or pattern than the barrier component material 24; as a non-limiting example, the base layer 12 may have a first color (e.g., a blue color), a dark color, or a specific color on a color scale and the subassembly (or the barrier component of the subassembly) may have no color (e.g., white), a second color (e.g., a light color), or a specific color on a color scale that contrasts with the first color.

As illustrated in FIG. 3, the subassemblies 22 are applied in position on the continuous base web 12 so that the at least two opposed edges 22A and 22B of a subassembly are aligned with the two opposed edges 12A and 12B of the continuous base web 12 to define repeating portions 42 that incorporate the subassemblies (also referred to as barrier panel portions 42) and alternating portions 44 that lack such subassemblies (also referred to as fold protection panel portions 44).

The process includes the step of providing one or more side tabs 46. These side tabs 46 are registered in position on the moving, continuous base web 12 with respect to at least one edge of the portions 42 that incorporate the subassemblies 22. For example, the side tabs may be accelerated and registered in position. Generally speaking, the side tabs 46 are formed by unwinding a material 48 from a supply roll 50 which travels in the direction indicated by the arrow associated therewith as the supply roll 50 rotates in the direction of the arrows associated therewith. The side tabs 46 may include optional barrier panel attachment means that may be applied to the side tabs 46 before the side tabs are applied to the continuous web 12. The material 48 may be separated in a cutting operation 52 to form the side tab s 46 and transferred to a combining roll 54 or other operation to register and place the side tab(s) onto the continuous web 12. The combining roll 54 holds the side tabs 46 on the drum surface using conventional techniques such as, for example, suction. Other techniques may be used to register the side tabs in position and transfer it to the base web. These include transfer pucks, belt placement assemblies or the like. Alternatively, a stack of individual side tabs 46 may be provided and the individual side tabs 46 may be fed to the combining roll (or other registration and transfer equipment using conventional techniques. The side tab 46 or a portion of the continuous web 12 that is to receive the side tab 46 may include a light coating of an adhesive (not shown) to maintain the subassembly in position on the continuous web 12.

Alternatively and/or additionally, the barrier panel attachment means may be applied to the barrier panel portion (not shown in the Figures).

These barrier panel attachment means may be adhesive tape, double-sided adhesive tape, cleavable release tapes, layered release tapes, cohesive materials, hook components of hook-and-loop fastening systems, mechanical fastening components including, but not limited to, snaps, clips, magnets, catches, slots and tabs, and combinations thereof. For example, the panel attachment means may be one or more lengths of adhesive tape having at least an end or portion that is stitched, ultrasonically bonded, thermo-mechanically bonded or adhered or adhesively bonded to the barrier panel or the side tab. It has been found that barrier panel attachment means may be a double sided tape having the same or different levels of adhesive or tack strength of adhesive on each side. Alternatively and/or additionally, the panel attachment means may have a double sided tape structure in which the central layer sandwiched by the adhesive is a splittable or separable material such as a splittable paper, splittable laminate, splittable foam, cleavable paper, cleavable release structure, cleavable foam or other cleavable or separable laminate. Exemplary splittable or cleavable materials are disclosed at, for example, U.S. Pat. No. 5,702,555 issued to Caudal et al. on Dec. 30, 1997; U.S. Pat. No. 4,310,127 issued to Frye on Jan. 12, 1982; U.S. Pat. No. 3,675,844 issued to Sorrell on Jul. 11, 1972; and U.S. Pat. No. 2,205,956 issued to Humphner on Jun. 25, 1940; the contents of which are incorporated by reference. According to an aspect of the invention, the panel attachment means may be in the form of an adhesive fastening tab or tape closure system such as the various types frequently used on diapers, incontinent garments and similar products. An exemplary tape closure system may be found at, for example, U.S. Pat. No. 4,410,325 issued to Lare on Oct. 18, 1983; the contents of which are incorporated by reference. Another exemplary tape closure system may be found at, for example, U.S. Pat. No. 4,585,450 issued to Rosch et al. on Apr. 29, 1986; the contents of which are incorporated by reference. As another example, the panel attachment means may be a length of fabric such as nonwoven fabric having an end or portion that is stitched, ultrasonically bonded, thermo-mechanically bonded or adhered or adhesively bonded to the barrier panel and/or the side tab and having a hook fastener from a hook and loop fastening system joined to the other end. It is contemplated that the base web and/or the barrier panel portion itself may function as the loop component of a hook and loop fastening system such as hook and loop fastenings systems available as VELCRO® brand fastener products from Velcro Industries B. V. Other exemplary hook systems may be used such as the hook system described in U.S. Pat.

No. 5,315,740 issued to Nestegard which relates to hooks having small dimensions so they engage low cost loop materials such as nonwoven webs. It is contemplated that various elements or components of the panel attachment means, may be integrally formed, such as by molding, co-extrusion or the like, along with any associated substrate layer. For example, the individual hook elements may be integrally formed simultaneously with a hook base-layer by coextruding the base layer and hook elements from substantially the same polymer material.

The subassemblies 22 and the side tabs 46 enter bonding station 55 where they are permanently attached to the continuous base web 12 to form a continuous work-piece 56. With respect to at least the subassemblies 22, the subassemblies 22 are desirably joined at or adjacent the edges 12A and 12B of the base web 12. The attachment may be a complete seam or the attachment may be partial along only one or a few portions of the edges. Alternatively and/or additionally, the attachment may be intermittent or discontinuous along all or a portion of each respective edge. Of course, other edges may also be attached or the layers may be attached together across all or portions of their entire surface area. The side tabs 46 are desirably attached in similar manners.

Referring to FIGS. 3, 4A, 4B and 5, this continuous work-piece 56 has two opposed edges 56A and 56B and barrier panel portions 42 coinciding with the subassemblies 22 and fold protection panel portions 44 coinciding with the portions lacking subassemblies. The continuous work-piece 56 has a first surface 58 including the subassemblies 22 and an opposed second surface 60. The subassemblies 22 and/or side tabs 46 may be attached to the continuous base web utilizing ultrasonic bonding techniques. Alternatively and/or additionally, thermal bonding, adhesive bonding, stitching, mechanical engagement or the like may be used to attach these components together. The subassemblies and/or side tabs may be attached to the continuous base web in sequence. For example, the subassemblies may be attached to the moving continuous base web and then the side tabs may be attached to the moving continuous base web. Alternatively, the subassemblies and side tabs may be attached to the continuous base web simultaneously. The individual side tabs 46 may be attached to the first surface 58, the second surface 60, or to both the first and second surfaces 58 and 60. In an aspect of the invention, the step of providing side tabs may include providing side tabs having barrier panel attachment means.

According to an aspect of the invention, the process 10 may include the step of adding indicia 62 to the barrier panel, the indicia identifying an upper boundary of a content receiving region of the barrier panel. A non-limiting example of indicia 62 placement is shown in FIG. 4A. The indicia 62 may be added to the subassembly 22 before the subassembly 22 is attached to the continuous base web 12. Alternatively and/or additionally, the indicia 62 may be added to the barrier panel portion 42 of the continuous work-piece 56 after the subassembly is attached to the continuous work-piece. In yet another aspect, the indicia may be added to the barrier panel of the multi-panel sterilization assembly. The indicia may be in a variety of forms include lines, broken lines, imprinted bonding patterns, logos and other printed matter. Thus the indicia could be wording such as "KIMBERLY-CLARK" or "KIMGUARD®" or "SMARTFOLD®".

The process of the present invention may further include the step registering at least one pull tab 64 in position on the barrier panel portion 42 of the moving, continuous base web 12 or the work-piece 56, and then attaching the pull tab 64. For example, the pull tab 64 may be accelerated and registered in position. Generally speaking, the pull tabs 64 are formed by unwinding a material 64B from a supply roll 64C which travels in the direction indicated by the arrow associated therewith as the supply roll 64C rotates in the direction of the arrows associated therewith. The material 64B may be separated in a cutting roll arrangement 64D and transferred to a combining roll 64E or other operation to register and place the pull tab(s) 64 onto the continuous web 12 or the work-piece 56. The combining roll 64E holds the pull tabs 64 on the drum surface using conventional techniques such as, for example, suction. Other techniques may be used to register the pull tabs in position and transfer it to the base web. Alternatively, a stack of individual pull tabs 64 may be provided and the individual pull tabs 64 may be fed to the combining roll 64E (or other registration and transfer equipment) using conventional techniques. The pull tab 64 or a portion of the continuous web 12 or the work-piece 56 that is to receive the pull tab 64 may include a light coating of an adhesive (not shown) to maintain the pull tab 64 in position on the continuous web 12 or the work-piece 56.

The pull tab 64 may be attached to the second surface 60 or the first surface 58. It is contemplated that the pull tab may be attached to both the first and second surfaces. According to the invention, the pull tab may desirably be attached to the moving, continuous base web along with the subassemblies and the side tabs. Alternatively and/or additionally, the process may involve the step of registering in position and attaching at least one pull tab in position on the barrier panel of an individual multi-panel sterilization assembly either before or after the individual assembly is separated from the continuous work-piece.

As shown in FIG. 5, portions of the edges 56A and 56B of the continuous work-piece 56 may be cut to create a shape prior to the step of separating the continuous work-piece 56 into individual multi-panel sterilization assemblies. For example, portions of the continuous work-piece 56 may be cut out from the two opposed edges 56A and 56B toward the longitudinal centerline L prior to the step of separating the continuous work-piece into individual multi-panel sterilization assemblies. The portions may be cut utilizing a rotary knife or other techniques, including but not limited to, a rotary die, lasers, water jets or the like.

The continuous work-piece 56 is then separated via a conventional cutting operation 66 into individual multi-panel sterilization assemblies 68, each multi-panel sterilization assembly including a barrier panel, a fold protection panel, and at least one side tab. Each may further include indicia and one or more pull tabs as well as other features. Of course, it is contemplated that one or more features such as side tabs, indicia and/or pull tabs may be omitted.

The process of the present invention may further include the step of collating multi-panel sterilization assemblies into a stack and folding the stack. In an aspect of the invention, the multi-panel sterilization assemblies include reinforcement elements and at least one pull tab and the multi-panel sterilization assemblies are collated so that the barrier panels are superposed in the stack. Referring to FIGS. 6A and 6B, there is shown in side perspective view (FIG. 6A) and in side cross-section view (FIG. 6B), not necessarily to scale, a stack 70 of multi-panel sterilization assemblies 68 collated so the barrier panels (i.e., barrier panel portions 42) are superposed. As can be seen, the reinforcement elements 40 and pull tabs 64 create a separation between adjoining multi-panel sterilization assemblies 68 in the stack 70 for a user to insert one or more fingers to grip one or more individual multi-panel sterilization assemblies 68 in the stack 70.

The present invention encompasses a process for making a stack of multi-panel sterilization assemblies. That is, the above-described process may be used to produce a collated stack of multi-panel sterilization assemblies including include reinforcement elements and at least one pull tab such that the reinforcement elements 40 and pull tabs 64 are arranged to create a separation between adjoining multi-panel sterilization assemblies 68 in the stack 70 for a user to insert one or more fingers to grip one or more individual multi-panel sterilization assemblies 68 in the stack 70.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

What is claimed is:

1. A continuous process for making a multi-panel sterilization assembly, the process comprising the steps of:
   providing a moving, continuous base web having a longitudinal centerline and two opposed edges generally parallel with the centerline;
   providing a plurality of subassemblies, each subassembly comprising at least two opposed edges and a barrier component that spans between the at least two opposed edges;
   applying the subassemblies in position on the moving, continuous base web such that the at least two opposed edges of each subassembly are aligned with the two opposed edges of the continuous base web to define repeating portions that incorporate the subassemblies and alternating portions that lack such subassemblies;
   providing side tabs;
   applying the side tabs in position on the moving, continuous base web with respect to at least one edge of the portions that incorporate the subassemblies;
   attaching the subassemblies and the side tabs to the moving, continuous base web to form a continuous work-piece having two opposed edges, a longitudinal centerline, barrier panel portions coinciding with the subassemblies, and fold protection panel portions coinciding with the portions lacking assemblies, the continuous work-piece having a first surface including the subassemblies and an opposed second surface; and
   separating the continuous work-piece into individual multi-panel sterilization assemblies, each multi-panel sterilization assembly comprising a barrier panel, a fold protection panel and at least one side tab.

2. The process of claim 1 wherein the plurality of subassemblies are provided by unwinding a roll of material and cutting the material into individual subassemblies.

3. The process of claim 2, wherein at least one reinforcement element is included with each of the subassemblies.

4. The process of claim 1, wherein subassemblies and/or side tabs are attached to the continuous base web utilizing ultrasonic bonding techniques.

5. The process of claim 1, wherein subassemblies and/or side tabs are adhesively secured to the continuous base web prior to ultrasonic bonding.

6. The process of claim 1, further comprising the step of adding indicia to a subassembly before the subassembly is attached to the continuous base web, the indicia identifying an upper boundary of a content receiving region of each barrier panel.

7. The process of claim 1, further comprising the step of adding indicia to a barrier panel portion of the continuous work-piece after the subassembly is attached to the continuous work-piece, the indicia identifying an upper boundary of a content receiving region of each barrier panel.

8. The process of claim 1, wherein the side tabs are attached to the first surface and/or the second surface.

9. The process of claim 1, wherein at least one side tab that is attached to each barrier panel portion includes a barrier panel attachment means.

10. The process of claim 1, further comprising the step of applying at least one pull tab in position on the barrier panel portion of the moving, continuous base web and attaching the pull tab.

11. The process of claim 10, wherein the pull tab is attached to the moving, continuous base web along with the subassemblies and the side tabs.

12. The process of claim 1, further comprising the step of applying at least one pull tab in position on the barrier panel of an individual multi-panel sterilization assembly after the individual assembly is separated from the continuous work-piece and attaching the pull tab.

13. The process of claim 1, wherein portions of the continuous work-piece are cut out from the two opposed edges toward the longitudinal centerline prior to the step of separating the continuous work-piece into individual multi-panel sterilization assemblies.

14. The process of claim 1, further comprising the step of collating multi-panel sterilization assemblies into a stack and folding the stack.

15. The process of claim 14, wherein each multi-panel sterilization assembly includes at least one reinforcement element and at least one pull tab and the multi-panel sterilization assemblies are superposed in the stack, whereby the reinforcement elements and pull tabs create a separation between adjoining multi-panel sterilization assemblies in the stack for a user to insert one or more fingers to grip an individual multi-panel sterilization assembly in the stack.

16. A continuous process for making a multi-panel sterilization assembly, the process comprising the steps of:
   providing a subassembly comprising at least two opposed edges and a barrier component spanning between the two opposed edges;
   applying the subassembly in position on a discrete base web having a leading edge, a trailing edge, and two opposed edges generally perpendicular to the leading edge and trailing edge such that the at least two opposed edges of a subassembly are aligned with the two opposed edges of the base web to define a discrete work-piece comprising a barrier panel portion incorporating the subassembly and a fold protection panel portion lacking the subassembly, the work-piece having a first surface including the subassembly and an opposed second surface;
   providing at least one side tab; and
   applying the at least one side tab in position on the work-piece with respect to at least one edge of the barrier panel portion; and
   attaching the subassembly and the at least one side tab to the base web to provide a multi-panel sterilization assembly comprising a barrier panel, a fold protection panel and at least one side tab.

17. The process of claim 16, wherein at least one reinforcement element is included with the subassembly.

18. The process of claim 16, further comprising the step of applying at least one reinforcement element in position on the barrier panel of the multi-panel sterilization assembly and attaching the reinforcement element to the multi-panel sterilization assembly.

19. The process of claim 16, further comprising the step of adding indicia to the subassembly before the subassembly is registered in position on the base web, the indicia identifying an upper boundary of a content receiving region of the barrier panel of the multi-panel sterilization assembly.

20. The process of claim 16, further comprising the step of adding indicia to the barrier panel of the multi-panel sterilization assembly, the indicia identifying an upper boundary of a content receiving region of the barrier panel.

21. The process of claim 16, wherein the at least one side tab is attached to the first surface and/or the second surface.

22. The process of claim 16, wherein the at least one side tab includes a barrier panel attachment means.

23. The process of claim 16, wherein subassembly and/or the at least one side tab are adhesively secured to the discrete base web prior to attaching.

24. The process of claim 16, further comprising the step of cutting and removing portions from one or more edges of the work-piece or the multi-panel sterilization assembly to create additional edges in the multi-panel sterilization assembly.

25. The process of claim 16 wherein portions of the multi-panel sterilization assembly are cut to create additional edges in the multi-panel sterilization assembly.

26. The process of claim 16, further comprising the step of collating multi-panel sterilization assemblies into a stack and folding the stack.

27. The process of claim 26, wherein the multi-panel sterilization assemblies include reinforcement elements and at least one pull tab and the multi-panel sterilization assemblies are collated so that the barrier panels are superposed in the stack, whereby the reinforcement elements and pull tab create a separation between adjoining multi-panel sterilization assemblies in the stack to provide a gap for a user to insert one or more fingers to grip one or more individual multi-panel sterilization assemblies within the stack.

* * * * *